United States Patent [19]
Farrell et al.

[11] Patent Number: 4,871,729
[45] Date of Patent: Oct. 3, 1989

[54] BISPLATINUM COMPLEXES AS CHEMOTHERAPEUTIC AGENTS

[75] Inventors: Nicholas Farrell, Winooski; Miles P. Hacker, Williston; John J. McCormack, Burlington; Sergio G. DeAlmeida, Winooski, all of Vt.

[73] Assignee: University of Vermont and State Agricultural College, Burlington, Vt.

[21] Appl. No.: 294,790

[22] Filed: Jan. 9, 1989

Related U.S. Application Data

[62] Division of Ser. No. 889,397, Jul. 25, 1986, Pat. No. 4,797,393.

[51] Int. Cl.$^4$ ............................................. A61K 31/555
[52] U.S. Cl. ..................................... 514/188; 514/492
[58] Field of Search ...................... 514/187, 188, 492; 556/24, 137; 546/5, 6

[56] References Cited

U.S. PATENT DOCUMENTS

| | | | |
|---|---|---|---|
| 4,225,529 | 9/1980 | Hydes et al. | 260/429 |
| 4,250,189 | 2/1981 | Hydes et al. | 424/287 |
| 4,533,502 | 8/1985 | Rochon et al. | 546/8 |
| 4,571,335 | 2/1986 | Taylor et al. | 424/131 |

Primary Examiner—Paul F. Shaver
Assistant Examiner—Stuart L. Hendrickson
Attorney, Agent, or Firm—Burns, Doane, Swecker & Mathis

[57] ABSTRACT

A bis-platinum complex having the structure:

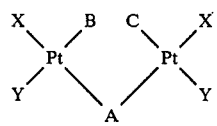

wherein X and Y are the same or different ligands and are halide, sulphate, phosphate, nitrate, carboxylate, substituted carboxylate or dicarboxylate. B and C are the same or different and are primary or secondary amines, or pyridine type nitrogens. A is a diamine or polyamine wherein the primary amine N atoms are coordinated to the Pt atom such that platinum is present as $Pt^{2+}$. The complexes are useful in the inhibition of tumors.

20 Claims, 1 Drawing Sheet

BISPLATINUM COMPLEXES AS CHEMOTHERAPEUTIC AGENTS

This application is a divisional, of application Ser. No. 889,397, filed July 25, 1986, now Pat. 4,797,393.

BACKGROUND OF THE INVENTION

The present invention relates to novel bis-platinum complexes and to pharmaceutical compositions containing them.

While cisplatin is widely used because of its antitumor activity, the search has continued for more powerful agents.

U.S. Pat. No. 4,225,529, discloses a cis coordinated compound of platinum having four ligands. (X, Y, A and B). The ligands X and Y are the same or different ligands selected from the group comprising a halide, sulphate, phosphate, nitrate, carboxylate, or substituted carboxylate and water. A and B are the same or different straight chain amines coordinated to the Pt through their N atoms, such that the platinum is represented by $Pt^{2+}$. The "diaquo compound" is formed by a literature method described in the *Indian Journal of Chemistry*, 8, 143 (1970).

U.S. Pat. No. 4,250,189, discloses platinum coordinated compounds of $Pt^{2+}$ or $Pt^{4+}$. The $Pt^{2+}$ compounds have four ligands, two of the ligands (X and Y) being selected from the group sulphate, phosphate, nitrate, carboxylate, or substituted carboxylate and water. The other two ligands are amines linked for example by an alkylene. The compound is contemplated for pharmaceutical use with a carrier.

U.S. Pat. No. 4,533,502, discloses platinum (II) compounds and their method of penetration. The starting compound is a cis - $[PtL_2-I_2]$ compound where L is an amine bonded to the Pt through the nitrogen and I is iodine. The starting compound is converted into cisplatinum (II) compounds similar to those in U.S. Pat. No. 4,225,529 above or a complex where two platinum (II) units are bridged by tetracarboxylate and each of the platinum (II) atoms are bonded to two of the carboxylate groups of the tetracarboxylate.

U.S. Pat. No. 4,565,884, describes a bis-platinum complex. The complex is linked by a central ligand with two pairs of acidic groups which could be carboxylates, sulphonates or phosphonates. The acids may be aromatic ring systems, alkyl cyclic ring systems or suitable aliphatic groups.

U.S. Pat. No. 4,571,335, discloses cis platinum (II) compounds that are usable for inhibiting herpes virus where the ligands include amines, dicarboxylic acids, and sulphonates The patents noted above discuss various Pt(II) and Pt(IV) compounds which have been found to have antitumor activity or pharmaceutical applications. The majority of these compounds are of the general formula cis-$[PtLL'X_2]$ or cis-$[PtLL'(X_2)(Y_2)]$ for the Pt (II) and Pt(IV) forming complexes, respectively. L normally represents amine ligands where X is normally a halogen and Y is normally hydroxy. Those bis-platinum complexes prepared in the patents above were linked through carboxylate bridges. The carboxylate linkage merely serves as a temporary carrier vehicle. Upon administration in pharmaceutical applications, such complexes undergo rapid hydrolysis to produce two cis monoplatinum moieties which are delivered to the active site. There is no recognition in the art of a pharmaceutically active form of a bis-diplatinum complex which is delivered as an intact bis complex to the active site.

Accordingly, it is an object of this invention to produce a stable bis-platinum complex for antitumor and pharmaceutical applications, the complex being resistant to chemical breakdown prior to engaging in its pharmaceutical function.

It is a further object of the present invention to produce an improved coordinated platinum complex, the complex exhibiting increased tumor inhibition.

A still further object is to provide a bis-coordinated platinum complex capable of being formulated for use in pharmaceutical functions.

SUMMARY OF THE INVENTION

The present invention is a bis-platinum complex having the structure:

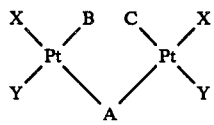

wherein X and y are the same or different ligands and are halide, sulphate, phosphate, nitrate, carboxylate, substituted carboxylate or dicarboxylate. B and C are the same or different and are primary or secondary amines, or pyridine type nitrogens. A is a diamine or polyamine wherein the primary amine N atoms are coordinated to the Pt atom such that platinum is present as $Pt^{2+}$.

DETAILED DESCRIPTION OF THE INVENTION

Figure 1:
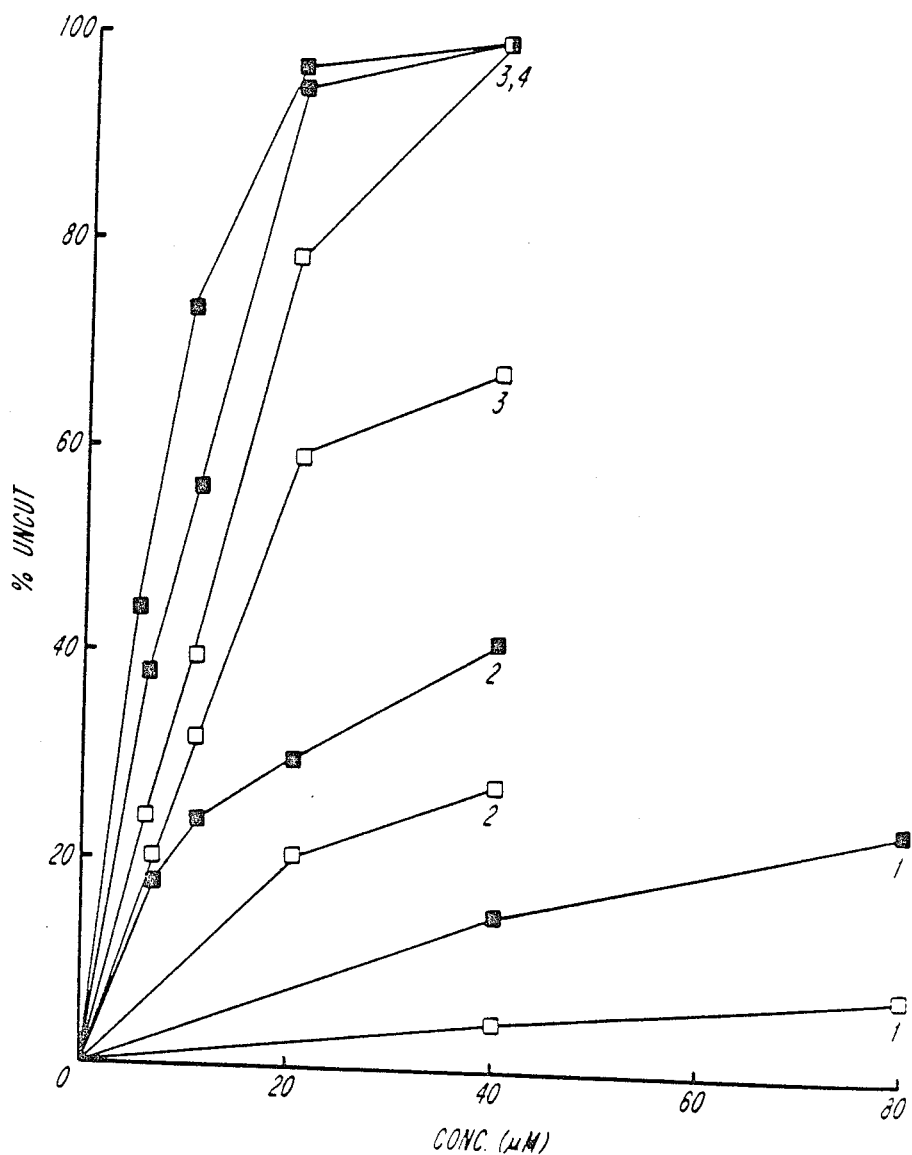
FIG. 1 is a graph illustrating inhibition of restriction enzymes Bam HI and EcoRI by complexes of the present invention versus inhibition by cisplatin.

The present invention relates to novel bis platinum (II and IV) complexes and methods for preparing such complexes.

According to a first aspect of the invention, there is obtained a bis platinum complex having the general structure

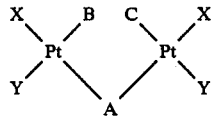

where X and Y are monodentate ligands or are combined as a bidentate ligand. B and C are the same or different amines, or pyridine type nitrogens. The bridging ligand A is a diamine or a polyamine.

X and Y when combined to form a bidentate ligand can comprise a dicarboxylate bidentate ligand, which may be substituted if desired. The dicarboxylates may be illustrated by the formula:

$(R^1R^2C)_k(CH_2)_l(COO)_2$ wherein $R^1$ and $R^2$ are the same or different, and are hydrogen, straight or branched alkyl of 1-5 carbon atoms, or hydroxy substituted alkyl, and k and l are the same or different and are an integer between 0 and 4, inclusive. Fused rings such as 1,1-cyclobutanedicarboxylate (CBDCA) are also useful. Preferred dicarboxylates are oxalate, malonate, or malonate substituted by methyl or hydroxyethyl.

When X and Y are represented by monodentate ligands they may be the same or different and may be halide, sulphate, phosphate, nitrate, carboxylate, or substituted carboxylate.

Where the X or Y groups are carboxylates or substituted carboxylates, they may be represented by the formula

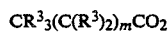

wherein m is an integer from 0 to 5, inclusive. The $R^3$ groups may be the same or different and may be hydrogen, substituted or unsubstituted straight or branched alkyl, aryl, alkaryl, aralkyl, alkenyl, cycloalkyl and cycloalkenyl, halogen, pseudohalogen, hydroxy, carbonyl, formyl, nitro, amido, amino, alkoxy, aryloxy, and sulphonic acid salts. Furthermore, the $R^3$ groups can be combined so that the two $R^3$ groups represent a doubly bonded oxygen or sulphur.

By lower alkyl and lower alkenyl in the present specification is meant one to five carbon atoms. By cycloalkyl is meant chains of 2–6 carbon atoms. By substituted in the present specification is meant substitution with a group chosen from aryl, cycloalkyl of 2 to 6 carbon atoms, cycloalkenyl, aralkyl, halogen, pseudohalogen, hydroxy, alkoxy, acycloamino, or carboxylic acid salts or esters of one to five carbon atoms.

The term "pseudohalogen" in this specification has the meaning found on page 560 of "Advanced Inorganic Chemistry" by Cotton and Wilkinson, Interscience Publishers, 1966. The text describes a pseudohalogen as being a molecule consisting of more than two electronegative atoms which, in the free state, represent halogens. Examples of these molecules are cyanide, cyanate, thiocyanate and azide.

The B and C amines are the same or different and can include ammonia, branched or straight chain lower alkyl amines, aryl amines, aralkylamines, lower alkenyl amines, cycloalkyl amines, cycloalkylenyl amines, and polycyclic hydrocarbon amines. Heterocyclic amines, nucleosides, nucleotides, pyridine-type nitrogen containing compounds, or amines with hydroxy, lower alkoxy, carboxylic acid or acid ester, nitro and halo substituents can be employed.

The bridging ligand A has the formula:

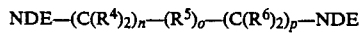

in which n and p are integers from 1 to 4, inclusive and o is 0 or 1; and the $R^4$ and $R^6$ groups are the same or different and are hydrogen, lower alkyl, aryl, cycloalkyl, cycloalkenyl, aralkyl, halogen, pseudohalogen, hydroxy, alkoxy, aryloxy, carboxylic acid ester, or carboxylic acid salt. Preferably all $R^4$ and $R^6$ groups are hydrogen.

The $R^5$ group is optional, and if employed is selected from alkyl, aryl (such as phenyl), amino, alkylamino, diamino of the formula:

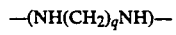

wherein q is an integer of 1 to 4, inclusive, hydroxyalkyl, alkoxy, sulfur or oxygen.

The D and E groups are the same or different and are selected from hydrogen, lower alkyl, aryl, alkaryl, aralkyl, alkenyl, cycloalkyl, cycloalkenyl, halogen, pseudohalogen, hydroxy, alkoxy, aryloxy, or sulphonic acids or salts thereof. The preferred substituent is hydrogen.

Particularly preferred A bridging ligands include straight chain diamines having the general formula:

wherein r is an integer from 2 to 12, inclusive. A second preferred embodiment contemplates the use of straight chain polyamines such as spermidine and spermine. These polyamines can be naturally occurring. Such naturally occurring polyamines can increase the solubility of the bis complex while simultaneously increasing the covalent binding of the complex.

In a second aspect of the invention there is provided a platinum (IV) bis complex having the structure

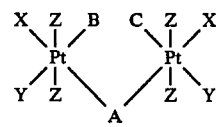

wherein the Z groups are the same or different and are selected from nitrate, halogen, pseudohalogen, or hydroxy, and X, Y, A, B, and C are as defined above. The preferred anions of Z are hydroxy and chloro.

The bis platinum complexes according to the present invention are intended for pharmaceutical application. The complex is useful for the treatment of the same diseases and modalities in the same patients as cisplatin. This includes the treatment of tumors, radiation sensitization or potentiation (Douple et al, "Cisplatin, Current Status and New Developments," Eds. A. W. Prestayko, S. T. Crooke, and S. K. Carter, Academic Press, 125 (1980); Douple, Platinum Metals Rev., 29, 118 (1985)), and parasitic diseases such as sleeping sickness (Farrell et al, Biochem. Pharmacology, 33, 961 (1984)). The complexes of the present invention are administered at approximately the same dosage levels as cisplatin, while taking into account their $LD_{50}$ values. The complex is normally associated with a suitable pharmaceutically acceptable carrier. For example, the complex and carrier can be formulated for parenteral or oral administration by methods well known in the art.

In order to further illustrate the present invention and the advantages thereof, the following specific examples are given, it being understood that these examples are intended only to be illustrative without serving as a limitation on the scope of the present invention.

The examples describe the preparation of the complexes by reaction of K[PtCl$_3$(NH$_3$)] with the bridging ligand. The K[PtCl$_3$(NH$_3$)] compound is prepared by the general method of T.S. Elleman et al, J. Amer. Chem. Soc., 80, 536 (1958). For amines other than NH$_3$, i.e., K[PtCl$_3$(amine)], the general procedure of Pasini et al, Inorg. Chim. Acta, 93, 167 (1984), incorporated herein by reference, is preferred.

EXAMPLES 1-10

Preparation of [{PtCl$_2$(NH$_3$)}$_2$H$_2$N(CH$_2$)$_r$NH$_2$] Complexes

K[PtCl$_3$(NH$_3$)] was slurried in a methanol solution in the ratio of 536.2 mg (1.5 mmol) to 5 ml of the methanolic solution. To a methanolic suspension of K[PtCl$_3$(NH$_3$)] is added a methanolic solution of the appropriate diaminoalkane (0.75 mmole in 30 millimeters). The mixture is stirred for 24 hours. The product bis complex forms an insoluble precipitate. Then the mixture is filtered using a sintered glass filter of medium porosity to obtain a creamish solid. The precipitate is washed with approximately five ml of water and twice with approximately five ml of methanol. The washed product is then dried in vacuo for approximately two hours at a temperature of approximately 50°-60° C.

The above procedure was repeated for straight chain diaminoalkanes of the general formula [H$_2$N(CH$_2$)$_r$NH$_2$] with the number r being an integer of 3 to 12, inclusive.

The complexes formed were white to cream solids. The complexes were sparingly soluble in water and alcoholic solvents and soluble in polar solvents such as dimethylsulfoxide (DMSO), dimethylformamide (DMF) and diemthylacetamide (DMA). Certain of the precipitated complexes formed by the reaction were subjected to elemental analysis. The data in Table I summarizes the results for the [{PtCl$_2$(NH$_3$)}$_2$H$_2$N(CH$_2$)$_r$NH$_2$] complexes:

TABLE I

ELEMENTAL ANALYSES FOUND (CALCULATED)

| r | % C | % H | % N | % Cl |
|---|---|---|---|---|
| 2 | 4.04 (3.83) | 2.34 (2.23) | 8.63 (8.94) | 22.12 (22.68) |
| 3 | 5.60 (5.62) | 2.41 (2.50) | 8.68 (8.75) | |
| 4 | 7.65 (7.33) | 2.84 (2.75) | 8.35 (8.56) | 21.53 (21.72) |
| 5* | 10.11 (10.28) | 3.14 (3.42) | 7.87 (8.00) | 19.99 (20.28) |
| 6 | 10.15 (10.55) | 2.93 (3.22) | 6.68 (8.21) | |
| 7 | 11.93 (12.06) | 3.47 (3.44) | 7.90 (8.04) | |
| 8 | 13.35 (13.52) | 3.70 (3.66) | 7.63 (7.88) | |
| 9 | 15.58 (14.91) | 4.03 (3.86) | 7.37 (7.73) | |
| 10 | 16.82 (16.26) | 4.14 (4.06) | 7.12 (7.59) | |
| 12 | 19.86 (18.79) | 4.60 (4.43) | 7.02 (7.31) | |

*Calculated with one mole of methanol of recrystallization.

Additionally, characterization data was obtained from infrared spectra. The tests were run on KBr disks. The data obtained corresponded to that of a cis configuration of the chlorides on each platinum atom. Representative wavelength values of Pt-Cl coordination are 326, 318(sh)cm$^{-1}$, for the r=4 derivative, and 330, 310(v.b.)cm$^{-1}$, for the r=5 derivative. Values (in cm$^{-1}$) for other derivatives are 326, r=6; 329, r=7; 328, r=8; 328, r=9; 328, r=10; and 325, r=12.

EXAMPLES 11 AND 12

Pt(IV) complexes were formed by oxidation with H$_2$O$_2$. The preparation was carried out by a standard procedure described by Kuoroda et al, Inorg. Chem., 22, 3620 (1983), incorporated herein by reference. The Pt(II) complexes were oxidized by this standard procedure to yield a Pt(IV) complex having the general formula [{PtCl$_2$(OH)$_2$NH$_3$}$_2$H$_2$N(CH$_2$)$_r$NH$_2$]. This procedure was performed on the r=5 and r=7 complexes of Examples 4 and 6 above.

Elemental analysis of these two complexes yielded the results set forth in Table II.

TABLE II

ELEMENTAL ANALYSES FOUND (CALCULATED)

| r | % C | % H | % N |
|---|---|---|---|
| 5 | 8.15 (8.17) | 3.25 (3.39) | 7.60 (6.62) |
| 7 | 10.99 (11.87) | 3.66 (3.76) | 7.32 (6.36) |

The I.R. spectrographic data on these complexes were similar to that of their respective Pt(II) starting complexes, except for slightly higher values of 336 cm$^{-1}$ for r=5 and 331 cm$^{-1}$ for r=7. The Pt(IV) complexes obtained from the H$_2$O$_2$ are also characterized by the presence of a broad band centered at approximately 540-560 5cm$^{-1}$. This additional band is attributable to the $\nu$ (Pt-OH).

The Pt(II) and Pt(IV) complexes according to the invention were tested for cytotoxicity activity against L1210 murine leukemia cells. The tests were carried out in vitro according to the procedures outlined by M.P. Hacker et al in Cancer Research, 45, 4748 (1985). The results in Table III are expressed as the ID$_{50}$ which represents the minimum dose required to cause 50% tumor inhibition.

TABLE III

TUMOR INHIBITION DATA

| r | ID$_{50}$ ($\mu$g/ml) |
|---|---|
| 2 | >10 |
| 4 | 1.4, 2.3 |
| 5 | 2.1, 3.0 |
|  | 0.36 (10% DMSO) |
| (Pt(IV)) | 3.2, 6.0 |
| 7 | 2.8 |
| 7 Pt(IV)) | 3.9 |
| 8 | 2.6 |
| 9 | 1.2 |
| 10 | 1.6 |
| 12 | 3.0 |

In the same system, but in cisplatin-resistant cell line, the r=5 derivative gave values of 4.3 and 9.3 $\mu$g/ml and thus is considered active against this line. For comparison, cisplatin gives ID$_{50}$ values of 0.1-02 $\mu$g in the sensitive line and 5-7 $\mu$g in the resistant line, denominated L1210/DDP. Thus the approximately 50-fold resistance of cisplatin is reduced to 2-3 fold in the bisplatinum series. The Pt(IV) complexes were run in water, the Pt(II) complexes in DMSO or 10% DMSO where indicated.

The Pt(II) complexes were also tested against L1210 tumors in BDF$_1$ mice. The results of these tests are expressed in %T/C, which represents the percentage of tumor weight in treated mice versus that in control mice. Again the method of testing was in accordance with the procedure published by M.P. Hacker et al, in Cancer Research, 45, 4748 (1985). The dosages were administered intraperitoneally in a suspension of hydroxypropylcellulose (HPC). The results are represented in Table IV.

TABLE IV

| r | Dose (mg/kg) | Schedule (days) | % T/C |
|---|---|---|---|
| 4 | 6.25 | 1, 5, 9 | 135 |
|  | 12.5 | 1, 5 | Toxic |
| 5 | 25 | 1, 5 | 206 (30d) |
|  |  |  | 260 (60d) |
|  | 12.5 | 1, 5 | 163 |

*For the r = 5 derivative 1/6 survivors were found at 30 and at 60 days at the higher dose.

The complexes of the invention were further tested to compare their DNA binding versus that of standard cis platinum cis-[PtCl₂(NH₃)₂]. An assay was performed using the inhibition of restriction enzymes upon binding the complexes to linearized plasmid DNA.

The method was according to a standard procedure wherein cleavage by BamHI or Eco RI at the defined sites results in only 2 fragments per enzyme since purified linear plasmid is used. DNA (20 mg/ml) in tris Cl(100 mM)-EDTA (1mM), pH 8 was exposed to complexes (usually 100 mM) for 1 hour at 37° C., after which unbound drug was removed using a spin-column of G-50 Sephadex (Pharmacia). Buffer (3.5 μl of 0.33M tris-acetate (pH7.9), 0.66M potassium acetate, 0.10M magnesium acetate, 0.005M dithiotheitol, 1 mg/ml bovine serum albumin) and 10 units of enzyme were added to eluted DNA (30 μl). EDTA (1 μl, 0.5M) was used to stop enzyme activity after 30 min, 37° C.; and tracking dye (7 μl:0.25% bromophenol blue, 0.25% xylene cyanol, in 30% glycerol water) was added. 10 μl of resulting solution was loaded onto a 1% agarose gel, made with E buffer (0.40 M Tris, 0.005 M sodium acetate, 0.001 M EDTA, pH to 7.8 with glacial acetic acid) and subjected to horizontal electrophoresis at 25V. The slab gel was stained with aqueous 1:10000 ethidium bromide solution (1 ng/ml) and photographed under UV light with an MP-4 Polaroid camera.

Inhibition of restriction enzymes BamHI and Eco RI was assessed qualitatively by noting the relative proportions of bands (cleaved vs uncleaved) or quantitatively by densitometer (Kipp & Zonen DD2) scan of the negative of the recorded picture.

The results are summarized in FIG. 1. Complex 1 represents trans-[{PtCl₂(DMSO)}₂H₂N(CH₂)₄NH₂], Complex 2 is the standard reference cis platinum complex displatin, and Complexes 3 and 4 are the bis-Pt(II) complexes according to Examples 4 (5=5) and 3 (r=4), respectively. Complex 1 represents a trans configuration analog of Complex 4.

The results signified by FIG. 1 clearly demonstrate the increased inhibition of endonuclease activity of the bis complexes according to the invention as compared to a standard monoplatinum complex. Therefore, the bis complexes show significantly increased effectiveness at binding DNA. The results of this test would apply equally to bisplatinum complexes linked by carboxylate bridges which merely serve to deliver two monoplatinum complexes, such as cisplatin, to the point of inhibition.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A method of inhibiting tumor growth in a mammal comprising the administration to the mammal of a tumor-inhibiting amount of a bis-platinum complex having the structure:

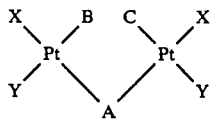

in which X and Y are the same or different ligands and are halide, sulphate, phosphate, nitrate, carboxylate, substituted carboxylate, or dicarboxylate; B and C are the same or different groups selected from primary and secondary amines and pyridine type nitrogens; and A is a diamine or polyamine wherein the primary amine N atoms are coordinated to the Pt atom such that platinum is present as $Pt^{2+}$.

2. A method of inhibiting tumor growth in a mammal comprising the administration to the mammal of a tumor-inhibiting amount of a bis-platinum complex having the stucture:

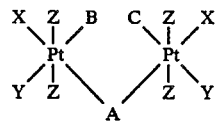

in which X and Y are the same or different ligands and are halide, sulphate, phosphate, nitrate, carboxylate, substituted carboxylate, or dicarboxylate; B and C are the same or different groups selected from primary and secondary amines and pyridine type nitrogens; the Z groups are the same or different and are nitrate, halogen, pseudohalogen, or hydroxy; and A is a diamine or polyamine wherein the primary amine N atoms are coordinated to the Pt atom such that platinum is present as $Pt^{4+}$.

3. The method of claim 1 wherein in the structure of the complex A has the formula:

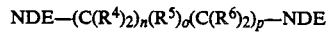

wherein n and p are integers from 1 to 4, inclusive and o is 0 or 1; $R^4$ and $R^6$ are the same or different and are hydrogen, lower alkyl, aryl, cycloalkyl, cycloalkenyl, aralkyl, halogen, pseudohalogen, hydroxy, alkoxy, aryloxy, carboxylic ester, or carboxylic acid salt; D and E are the same or different and are hydrogen, lower alkyl, aryl, alkaryl, aralkyl, alkenyl, cycloalkyl, cycloalkenyl, halogen, pseudohalogen, hydroxy, alkoxy, aryloxy, sulphonic acid, or sulphonic acid salt; and $R_5$ is alkyl, aryl, amino, alkylamino, or diamino of the formula:

wherein q is an integer of 1 to 4, inclusive, hydroxyalkyl, alkoxy, sulfur or oxygen.

4. The method of claim 3 wherein o in the structure of the complex is 0, and $R_4$, $R_6$, D and E are all hydrogen.

5. The method of claim 1 wherein in the structure of the complex X and Y are all chlorine and B and C are amines.

6. The method of claim 4 wherein in the structure of the complex X and Y are all chlorine and B and C are amines.

7. The method of claim 1 wherein in the structure of the complex A is a naturally occurring polyamine.

8. The method of claim 7 wherein the polyamine is spermidine or spermine.

9. The method of claim 1 wherein in the structure of the complex A is $H_2N-(CH_2)_r-NH_2$, and r is an integer from 2 to 12, inclusive.

10. The method of claim 1 wherein in the structure of the complex X and Y are carboxylates or substituted carboxylates of the formula:

$$CR^3{}_3(C(R^3)_2)_mCO_2$$

wherein m is an integer from 0 to 5, inclusive; and the $R^3$ groups are the same or different and are hydrogen, substituted or unsubstituted straight or branched alkyl, aryl, alkaryl, carboxylic acid ester, or carboxylic acid salt.

11. The method of claim 1 wherein in the structure of the complex X and Y combine to form a dicarboxylate of the formula:

$$(R^1R^2C)_k(CH_2)_l(COO)_2$$

wherein $R^1$ and $R^2$ are the same or different, and are hydrogen, straight or branched alkyl or hydroxy substituted alkyl of 1-5 carbon atoms; and k and l are the same or different and are each an integer between 0 and 4, inclusive.

12. The method of claim 11 wherein the dicarboxylate is oxalate, malonate, or malonate substituted by methyl or hydroxyethyl.

13. The method of claim 2 wherein in the structure of the complex Z is hydroxy or chloro.

14. The method of claim 2 wherein in the structure of the complex A has the formula:

$$NDE-(C(R^4)_2)_n(R^5)_o(C(R^6)_2)_p-NDE$$

wherein n and p are integers from 1 to 4, inclusive, and o is 0 or 1; $R^4$ and $R^6$ are the same or different and are hydrogen, lower alkyl, aryl, alkaryl, cycloalkyl, cycloalkenyl, aralkyl, halogen, pseudohalogen, hydroxy, alkoxy, aryloxy, carboxylic ester, or carboxylic acid salt and are the same or different and are hydrogen, lower alkyl, aryl, alkaryl, aralkyl, alkenyl, cycloalkyl, cycloalkenyl, halogen, pseudohalogen, hydroxy, alkoxy, aryloxy, sulphonic acid, or sulphonic acid salt, and $R^5$ is alkyl, aryl, amino, alkylamino, or diamino of the formula:

$$-(NH(CH_2)_qNH)-$$

wherein q is an interger of 1 to 4 inclusive, hydroxyalkyl, alkoxy, sulfur or oxygen.

15. The method of claim 13 wherein in the structure of the complex o is 0, and $R^4$, $R^6$, D and E are all hydrogen.

16. The method of claim 2 wherein in the structure of the complex X and Y are all chlorine and B and C are amines.

17. The method of claim 14 wherein in the structure of the complex X and Y are all chlorine and B and C are amines.

18. The method of claim 2 wherein in the structure of the complex A is a naturally occurring polyamine.

19. The method of claim 18 wherein in the structure of the complex the polyamine is spermidine or spermine.

20. The method of claim 2 wherein in the structure of the complex A is $H_2N-(CH_2)_r-NH_2$, and r is an integer from 2 to 12, inclusive.

* * * * *